United States Patent [19]

Rhoades

[11] Patent Number: 4,802,851
[45] Date of Patent: Feb. 7, 1989

[54] DENTAL APPLIANCE

[76] Inventor: Clark J. Rhoades, 181 Tweed Blvd., Nyack, N.Y. 10960

[21] Appl. No.: 152,033

[22] Filed: Feb. 3, 1988

[51] Int. Cl.⁴ ............................................. A61C 17/04
[52] U.S. Cl. ......................................... 433/93; 433/29; 433/140; 128/13
[58] Field of Search ...................... 433/93, 96, 140, 29; 128/13

[56] References Cited

U.S. PATENT DOCUMENTS

| | | | |
|---|---|---|---|
| 1,122,086 | 12/1914 | Dunlop | 433/29 |
| 2,937,445 | 5/1960 | Erickson | 32/33 |
| 3,049,806 | 8/1962 | Cofresi | 32/33 |
| 3,101,543 | 8/1963 | Baughan | 32/33 |
| 3,124,879 | 3/1964 | Van Lanigan | 32/33 |
| 3,217,708 | 11/1965 | Roberts | 128/136 |
| 3,225,444 | 12/1965 | Greenman | 32/33 |
| 3,344,523 | 10/1967 | Halsey | 32/33 |
| 3,396,468 | 8/1968 | Dayhoff | 32/33 |
| 3,426,430 | 2/1969 | Newman | 32/33 |
| 3,455,024 | 7/1969 | Gelarie | 32/33 |
| 3,456,348 | 7/1969 | Lanigan | 433/94 |
| 3,483,619 | 12/1969 | Smith | 32/40 |
| 3,557,456 | 1/1971 | Hutchinson | 32/33 |
| 3,722,101 | 3/1973 | Via | 433/140 |
| 3,864,831 | 2/1975 | Drake | 433/91 |
| 3,881,254 | 5/1975 | Epstein | 32/33 |
| 3,913,231 | 10/1975 | Orsing | 32/33 |
| 3,916,880 | 11/1975 | Schroer | 128/12 |
| 4,017,975 | 4/1977 | Johnson | 32/33 |
| 4,019,255 | 4/1977 | Cohen et al. | 32/33 |
| 4,053,984 | 10/1977 | Moss | 32/33 |
| 4,074,435 | 2/1978 | Orsing | 32/33 |
| 4,167,814 | 9/1979 | Schubert | 32/33 |
| 4,215,984 | 8/1980 | Reichley | 433/93 |
| 4,259,067 | 3/1981 | Nelson | 433/93 |
| 4,260,378 | 4/1981 | O'Neil | 433/93 |
| 4,325,695 | 4/1982 | Sundelin et al. | 433/93 |

Primary Examiner—Robert Peshock
Attorney, Agent, or Firm—John H. Crozier

[57] ABSTRACT

A combination jaw rest and ejector having a generally hollow wedge-shaped body with upper and lower channels in which a patient's teeth rest and which holds open the patient's mouth. The wedge-shaped body is placed in the patient's mouth on the side opposite that on which work is being performed. A suction hose is attached to the body and the side of the body facing the work site is perforated so that a relatively high volume of air may be drawn into the body through the suction hose, thus drawing, with the air, blood, spray, and debris and substantially preventing the discharge of these materials, which may carry disease transmitting factors, from the patient's mouth. In one embodiment, the body includes perforated salive collecting tube and/or a tongue depressor attached thereto. In a further embodiment, the body includes an illumination source therein to illuminate the interior of the patient's mouth. In another embodiment, a combination jaw rest and ejector includes an illumination source and is provided in a system which includes a combination air flow/light switch. In another embodiment, there is provided an illuminated jaw rest without means for evacuating material from the patient's mouth.

20 Claims, 3 Drawing Sheets

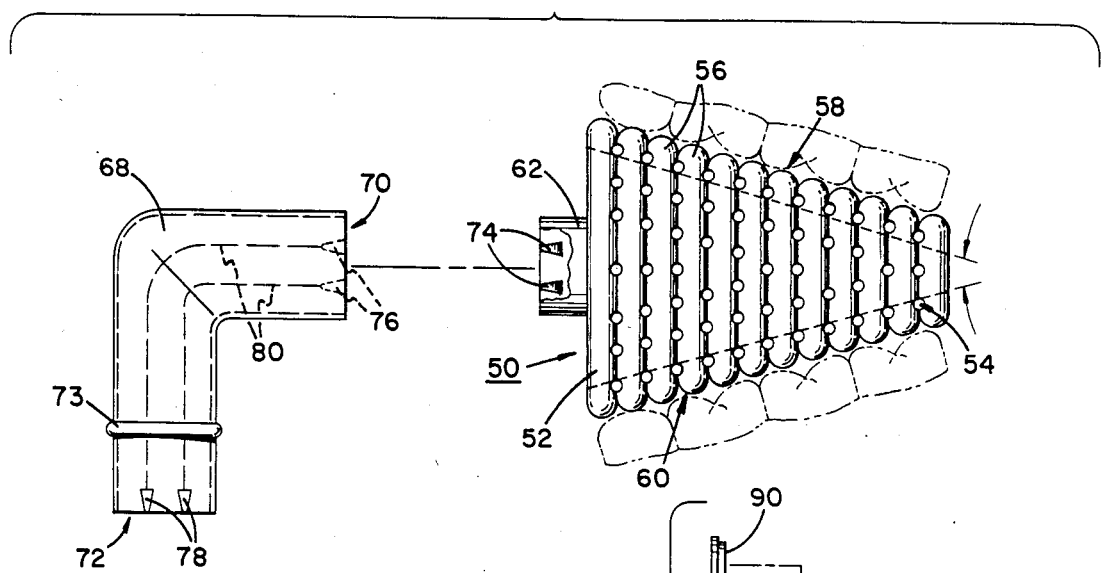
FIG. 1
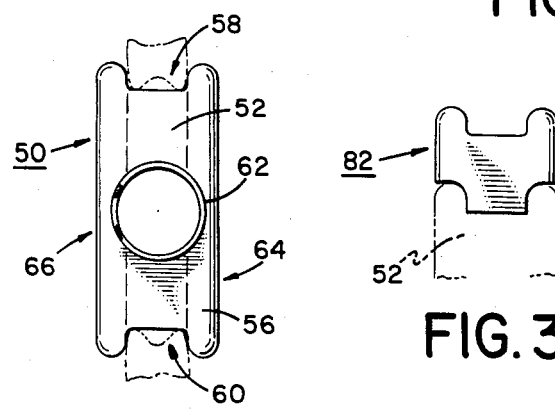
FIG. 2
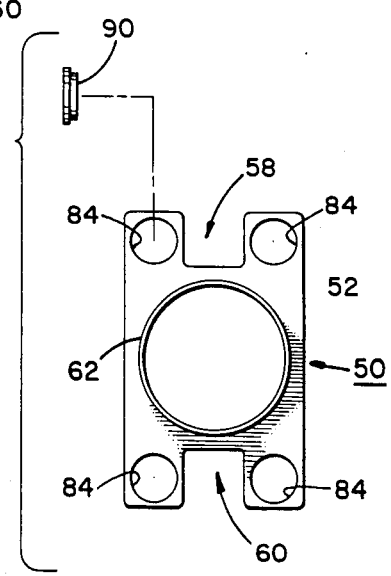
FIG. 3
FIG. 4
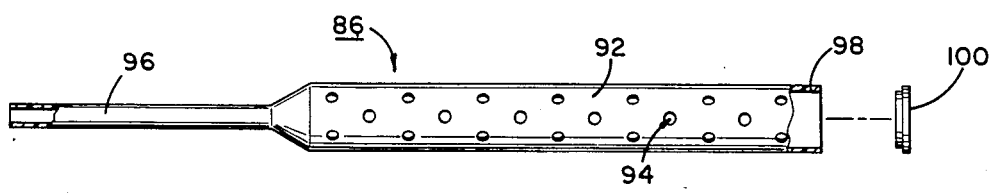
FIG. 5
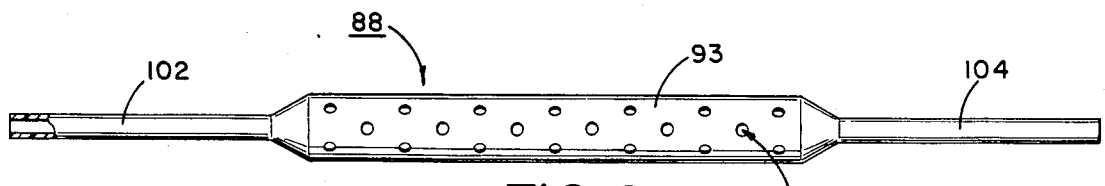
FIG. 6

FIG. 7
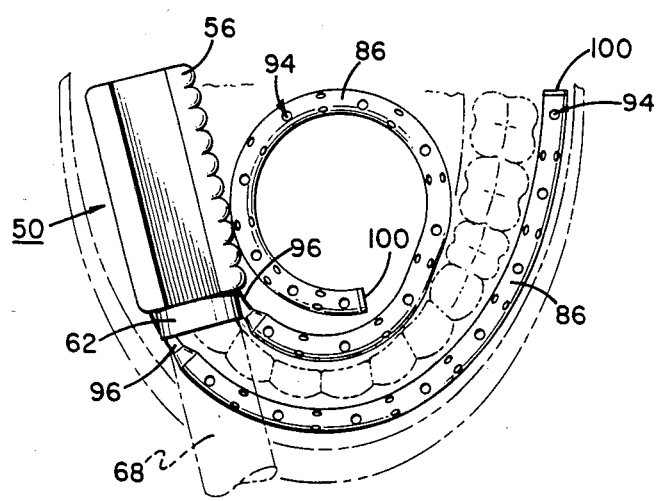
FIG. 8
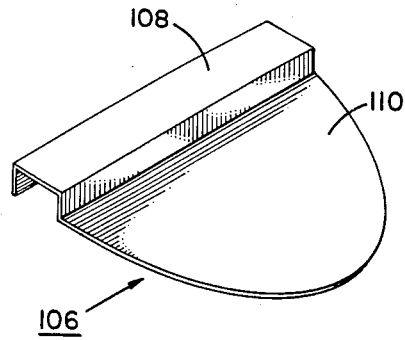
FIG. 9
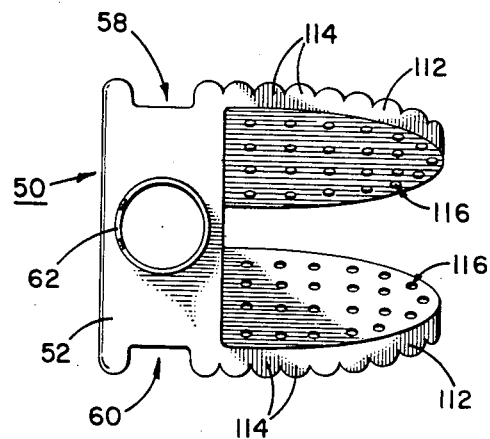
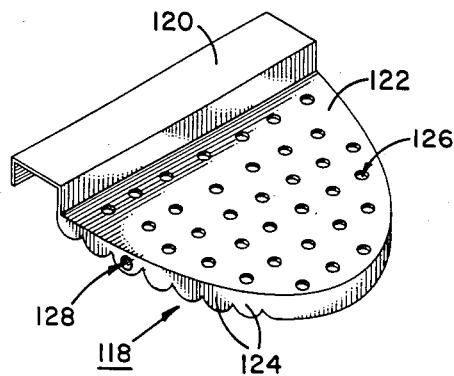
FIG. 10
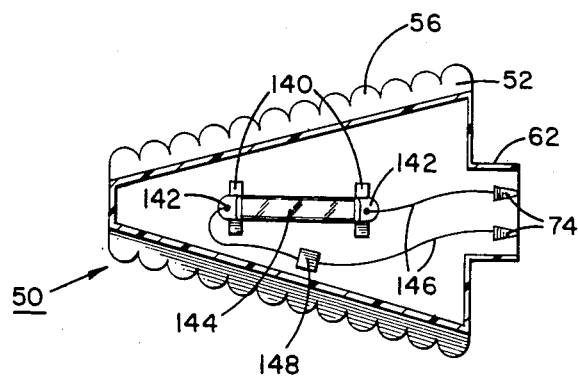
FIG. 11

DENTAL APPLIANCE

BACKGROUND OF THE INVENTION

1. Field of the Invention

The present invention relates to dental appliances in general, and, more particularly, to a dental appliance that combines a jaw rest with a high volume ejector that removes saliva, cooling water, blood, pumice, and spray from the mouth of a dental patient, thus not only removing these elements which contribute to patient discomfort, but also eliminating a means by which diseases such as AIDS may be transmitted from the patient to others.

2. Background Art

During dental and oral surgical procedures, the patient is typically in a supine or semi-supine position which causes saliva to accumulate in the mouth. This saliva is difficult to swallow because of the patient's position, because the patient's mouth is open, and because dental instruments are inserted in the patient's mouth. Additionally, modern high-speed cutting instruments usually require a stream of water to be directed onto the cutting surface for cooling. Further, blood and pumice may accumulate as a result of the dental or surgical procedures.

As anyone who has been a dental patient well knows, there is also a considerable amount of spray of saliva, blood, and other matter that exits the patient's mouth during many of the procedures. This spray, while being esthetically unpleasant, also has the more serious consequence of being a potential disease carrier. This places at risk, not only the doctor and any assistants present, but also places at risk subsequent patients who may come into contact with the airborne spray or with surfaces in the area which are contaminated with the spray but are not adequately sterilized between patients. It has become well known that, among other diseases, acquired immune deficiency syndrome (AIDS) may be communicated between humans by the transfer of blood.

A second problem that the dental patient and the doctor well know is the difficulty the patient has in keeping his mouth sufficiently open for relatively extended periods of time during the procedure. This increases the stress on the patient in an inherently stressful situation and provides for more difficult working conditions for the doctor and any assistants.

Both these problems have been addressed by various devices. The various conventional saliva ejectors generally adequately remove saliva, although sometimes from very localized areas of the mouth. Those that are not hand-held must be uncomfortably supported by the patient's lips or cheeks or the floor of the patient's mouth. All are limited in the volume of the oral cavity serviced and in the volume of air flow, so that none is directed to, or capable of, the collection of, and prevention of the escape of, spray from the patient's mouth. Many have the unpleasant disadvantage of being able to draw soft tissue of the patient's mouth into the suction device.

There have also been an number of jaw rest devices of varying design some of which have been combined with saliva ejectors. However, all of these ejectors suffer from the limitations described above.

Accordingly, it is a principal object of the present invention to provide a combination jaw rest and ejector that is comfortable and quickly and easily inserted in the patient's mouth.

An additional object of the present invention is to provide a combination jaw rest and ejector that substantially prevents the discharge of spray, blood, and debris from the patient's mouth.

A further object of the present invention is to provide a combination jaw rest and ejector that is adjustable to accommodate different mouth configurations and degrees of desired opening of the mouth.

Another object of the present invention is to provide a combination jaw rest and ejector that substantially prevents the sucking of soft tissue into the device.

Yet an additional object of the present invention is to provide a combination jaw rest and ejector that may be easily sterilized for reuse or is economical enough that it may be disposed of after a single use.

Yet a further object of the present invention is to provide a combination jaw rest and ejector that includes means for illuminating the interior of the patient's mouth.

Yet another object of the present invention is to provide a combination jaw rest and ejector system that includes illumination means and a combination air flow/light switch.

SUMMARY OF THE INVENTION

The present invention substantially overcomes the limitations of conventional jaw rests, ejectors, and combinations thereof by providing a combination jaw rest and ejector having a generally hollow wedge-shaped body with upper and lower channels in which the patient's teeth rest and which body holds open the patient's mouth. The wedge-shaped body is placed in the patient's mouth on the side opposite that on which work is being performed. A suction hose is attached to the body and the side of the body facing the work site is perforated so that a relatively high volume of air may be drawn into the body through the suction hose, thus drawing with the air blood, spray, and debris and substantially preventing the discharge of these materials which might otherwise carry disease transmitting factors from the patient's mouth. In one embodiment, the body includes perforated saliva collecting tubes and/or a tongue depressor attached thereto. In a further embodiment, the body includes an illumination source therein to illuminate the interior of the patient's mouth. In another embodiment, a combination jaw rest and ejector includes an illumination source and is provided in a system which includes a combination air flow/light switch. An additional embodiment provides only an illuminated jaw rest without means for evacuating materials from the patient's mouth.

BRIEF DESCRIPTION OF THE DRAWING

FIG. 1 is a side elevation view of a combination jaw rest and ejector of the present invention.

FIG. 2 is an end elevation view thereof.

FIG. 3 is an end elevation view of a spacer insert for use with the present invention.

FIG. 4 is an end elevation view of an alternative embodiment of the present invention.

FIGS. 5 and 6 are top plan views of saliva collecting tubes used with the embodiment of the present invention shown on FIG. 4.

FIG. 7 shows the embodiment of FIG. 4, including saliva collecting tubes, inserted in a patient's mouth.

FIG. 8 is a perspective view of a removable tongue depressor for use with the present invention.

FIG. 9 is an end elevation view of another alternative embodiment of the present invention, including integral tongue depressors.

FIG. 10 is a perspective view of another removable tongue depressor, adapted for spray removal.

FIG. 11 is a side elevation cross-sectional view of a further alternative embodiment of the present invention, having an illumination source therein.

DESCRIPTION OF THE PREFERRED EMBODIMENTS

Figure 12:
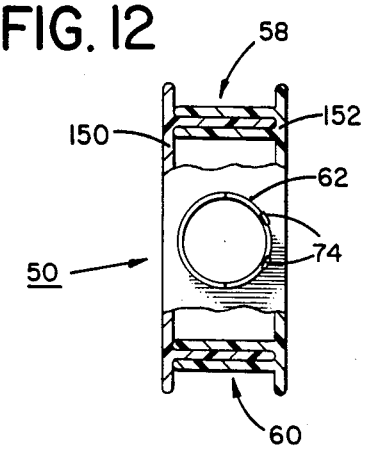
FIG. 12 is an end elevation view of an additional embodiment of the present invention having a sectionalized body.

Referring now to the Drawing, FIGS. 1 and 2 are side and end views, respectively, of the dental appliance of the present invention, generally indicated by the reference numeral 50, which includes a tapered, wedge-shaped body 52 having defined therein a plurality of perforations, as at 54. Perforations 54 are preferably located between scallops, as at 56, forming the sides of body 52. Perforations 54 may also be formed (not shown) on second side 66 of the body, if desired. Body 52 also defines first and second tooth channels 58 and 60, respectively, into which several of the patient's teeth removably rest when the body is inserted in the patient's mouth. For greater clarity, the patient's teeth (phantom), on FIG. 1, are not shown fully inserted in first and second tooth channels 58 and 60. A coupling 62 is disposed at the large end of body 52 for communication with the interior of the body. Also shown on FIG. 1 is angle tube 68 having first and second ends 70 and 72, respectively, with the first end adapted to fit grippingly over coupling 62 and second end 72 adapted to have a suction tube (not shown) fit grippingly over it. A raised annular ridge 73 may be circumferentially formed around angle tube 68 near second end 72 of the angle tube to aid in the sealing of the suction tube (not shown) which leads to a source of vacuum (not shown). Angle tube 68 is dimensioned so that second end 72 is located outside the patient's mouth when dental appliance 50 is inserted in the mouth. Angle tube 68 may be articulated or sufficiently flexible to conveniently position it in relation to the patient's mouth and the vacuum source. The suction tube may also be directly attached to coupling 62.

A pair of raised tapered male electrical connectors 74 may be formed on coupling 62, a pair of recessed tapered female electrical connectors 76 may be formed on first end 70 to mate with connectors 74, and a pair of raised male electrical connectors 78 may be formed on second end 72 to mate with a corresponding pair of recessed electrical connectors (not shown) formed on the end of the suction tube not shown). Pairs of electrical connectors 76 and 78 are electrically joined by means of a pair of conductors 80. The function of these electrical elements will be described later with reference to FIG. 11.

FIG. 3 is an end elevation view of a spacer, generally indicated by the reference numeral 82, which may be inserted into one or both of first and/or second tooth channels, 58 or 60, respectively, to cause the jaws of the patient to open to a wider position for a given placement of dental appliance 50.

FIG. 4 shows a side elevation view of the large end of body 52 in an alternative embodiment. Here, openings 84 which communicate with the interior of body 52 are defined in the large end thereof for the insertion of one or more of saliva collecting tubes, such as 86 and/or 88 shown on FIGS. 5 and 6, respectively. When it is not desired to use saliva collecting tubes such as 86 and/or 88 in all of openings 84, plugs, as at 90, may be inserted in the openings not being used for saliva collecting tubes. Alternatively, saliva tubes may be parmanently attached to body 52.

Referring now to FIGS. 5 and 6, each of saliva collecting tubes 86 and 88 are pliant hollow tubes each having formed in the walls of enlarged sections 92 and 93 thereof, respectively, a plurality of perforations, as at 94. Saliva tube 86 has a round small section 96 sized to fit into one of openings 84 and be held therein by friction. The distal end 98 of enlarged section 92 of saliva tube 86 may be cut to the desired length and then closed by tube plug 100. Alternatively, distal end 98 could be closed when manufactured to provide a fixed length (not shown). Saliva tube 88 has two small round sections 102 and 104 disposed at either end of the tube and each sized for friction fit into openings 84. One or both of the small sections 102 and 104 may be cut to provide a desired length and configuration for placing in the patient's mouth. Some length adjustment may also be achieved by sliding small sections 96, 102, and/or 104 to a greater or lesser extent into openings 84.

FIG. 7 is a top plan view of dental appliance 50 placed on the lower jaw of a patient, with two saliva collecting tubes 86, one coiled alongside, over, and under the patient's tongue and the other placed along the depression formed by the lower jaw teeth and the cheek. The latter saliva tube 86 also serves as a cheek retractor. Alternatively, or in addition, the small end of body 52 or either or both sides thereof may be adapted (not shown) for the connection of one or more saliva collecting tubes 88, the arrangement shown on FIG. 7 being only one of of many possible arrangements within the intent of the present invention. With dental appliance 50 in the position shown, the work site in the patient's mouth would be at the front of the mouth or on the side of the mouth opposite the appliance.

FIG. 8 is a perspective view of a removable tongue depressor, generally indicated by the reference numeral 106. Tongue depressor 106 has a channel portion 108 for a friction fit with the lower of first and second tooth channels 58 and 60, respectively. Resilient flap 110 holds the patient's tongue in position away from the work site.

FIG. 9 shows an alternative embodiment of the present invention in which dental appliance 50 includes hollow, integral tongue depressors 112 which may have scallops, as at 114, for comfortable contact with the patient's tongue and perforations, as at 116, for additional flow of air, spray, and saliva from the patient's mouth. The hollow interiors of tongue depressors 112 communicate with the hollow interior of body 50 for flow of air therebetween. Perforations 116 may be formed on both surfaces of tongue depressors 112, as shown on FIG. 9, or they may be formed on only one of the surfaces. Also, only one tongue depressor 112 may be provided.

FIG. 10 shows a scalloped removable tongue depressor having air flow capability, generally indicated by the reference numeral 118. Tongue depressor 118 has a channel portion 120 for a friction fit with the lower of first and second tooth channels 58 and 60, respectively, and flap portion 122 holds the patient's tongue in position away from the work site. Flap portion 122 is hollow and has perforations, as at 126, and an opening 128 for connection by a tube (not shown) to one of openings 84 in body 52. The tongue-contacting surface of depressor 118 is scalloped, as at 124, for patient comfort and may also be perforated (not shown).

FIG. 11 shows yet another embodiment of the present invention, this one incorporating means for illuminating the interior of the patient's mouth. Here, dental appliance 50 has pairs of studs 140 mounted to an interior wall of body 50. Pairs of studs 140 carry electrical contacts 142 between which a light bulb 144, preferably one of low wattage and low voltage, is mounted. Conductors 146 provide electrical connection to connectors 74 in coupling 62. When lit, bulb 144 will provide light through perforations 54. If body 52 is fabricated of a clear or translucent material, there will be provided even greater illumination of the patient's mouth. Air flowing through appliance 50 will cool bulb 144 and, if the wattage of the bulb is sufficiently high to cause discomfort to the patient when the air flow stops, a thermal cut-out switch 148 may be inserted in one of conductors 146 to turn off bulb 144 should the flow of air be stopped for any length of time.

It is also within the intent of the present invention to provide an illuminated jaw rest, generally as described above, but without means for evacuating material from the patient's mouth.

FIG. 12 shows an end elevation view of a sectionalized embodiment of the present invention, with dental appliance 50 having first and second body halves 150 and 152. As shown, first body half 150 fits into second body half 152 and is held therein by friction. Such an embodiment is particularly useful when dental appliance 50 includes an illuminating feature such as shown on FIG. 11 and also allows access to the interior of the appliance for cleaning and sterilization when the appliance is to be reused. Other means of access to the interior of dental appliance 50, known in the art, are within the contemplation of the present invention.

Figure 13:
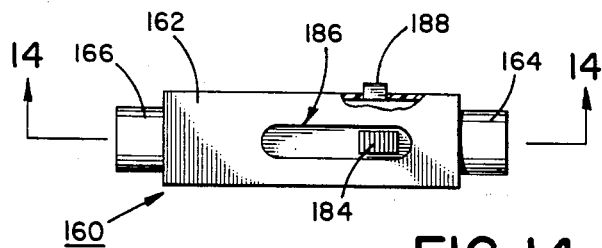
FIG. 13 is a top plan view and FIGS. 14 through 17 are cross-sectional views of a combination air flow/light switch which may be included in a system according to the present invention.
Figure 14:
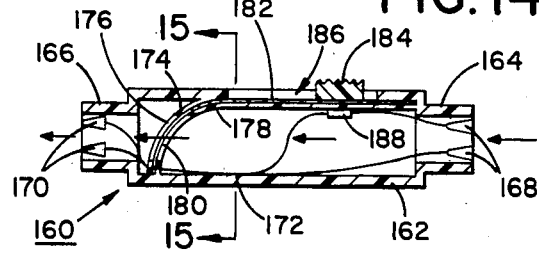
Figure 15:
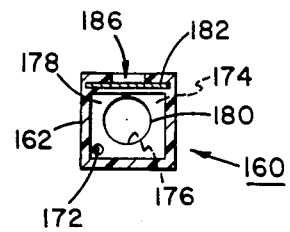
Figure 16:
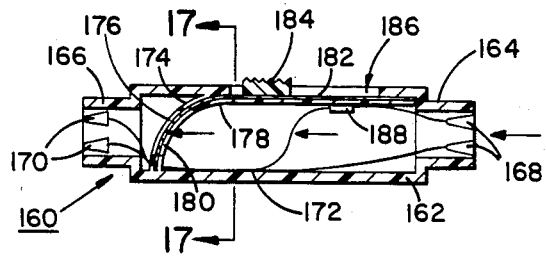
Figure 17:
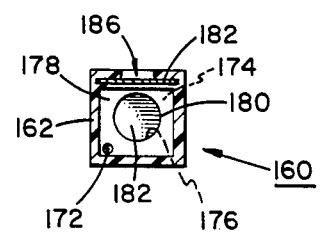

FIGS. 13 through 17 show a combination air valve/light switch, generally indicated by the reference numeral 160, with FIGS. 13, 14, and 15 showing the switch in the open/on position and FIGS. 16 and 17 showing the switch in the closed/off position. Switch 160 may be included with dental appliance 50 as part of a system and is intended to be placed at a convenient location in the suction hose (not shown) between angle tube 68 and the vacuum source (not shown). Switch 160 includes a generally hollow central body part 162 having air inlet and outlet ends 164 and 166, respectively, which have disposed therein, respectively, pairs of electrical contacts 168 and 170. Pairs of electrical contacts 168 and 170 have a pair of conductors 172 joining the conductors as shown. Inlet and outlet ends 164 and 166 and electrical contacts 168 and 170 engage corresponding elements of the suction tube (not shown). Disposed within hollow body 162 is a first flat curved wall 174, having a first aperture 176 and a second flat curved wall 178, having a second aperture 180 having substantially the same dimensions as first aperture 176; with first and second walls 174 and 178 being closely spaced apart and with the upper ends thereof being closer to air inlet end 164 than to air outlet end 166. Slidingly disposed between first and second walls 174 and 178 is a flexible gate 182 which is shown on FIGS. 13, 14, and 15 in a wide open position and on FIGS. 16 and 17 in a fully closed position. Fixedly attached to flexible gate 182 is an adjusting button 184 which extends through opening 186 in body part 162 for attachment to flexible gate 182 and which may be conveniently engaged by the thumb of a human operator (not shown). Positions of flexible gate 182 between those shown on FIGS. 14 and 15 and on 16 and 17 will modulate the flow of air through switch 160. Also included in body part 162 is a microswitch 188 serially electrically connected serially in one of conductors 172. When combination air valve/light switch 160 starts to move from its closed/off position shown on FIGS. 16 and 17, microswitch 188 closes thus turning on bulb 144 shown on FIG. 11, as soon as air flow starts.

The various elements of the present invention may be constructed of any suitable materials and by processes well known in the art. Body 52 is preferably constructed of a somewhat resilient elastomeric material such as polyethylene which affords a comfortable surface for the patient and is economical enough that the body may be disposed of after a single use. Polyethylene may also be sterilized for reuse by methods normally employed for sterilizing other appliances.

It will thus be seen that the objects set forth above, among those made apparent from the preceding description, are efficiently attained and, since certain changes may be made in the above constructions without departing from the scope of the invention, it is intended that all matter contained in the above description or shown in the accompanying Drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

I claim:

1. A combination jaw rest and ejector device, comprising:
   (a) a generally hollow, closed, wedge-shaped body having longitudinal upper and lower channels formed on the sloped upper and lower edges thereof, said body and said channels being dimensioned such that said body may be inserted into one side of a patient's mouth, with several upper teeth of said patient removably fitting into said upper channel and with several lower teeth of said patient removably fitting into said lower channel, such that said body holds open said patient's mouth;
   (b) a plurality of holes defined through at least one side of said body; and
   (c) communicating means to permit communication of said holes and the interior of said body with a source of vacuum;
whereby, airborne liquid and solid materials may be drawn from said patient's mouth, through said communicating means, and to said source of vacuum.

2. The device defined in claim 1, wherein said holes are disposed between scallops formed on said at least one side.

3. The device defined in claim 1, wherein a spacer may be removably placed in either of said upper and lower channels to cause the degree of opening of said patient's mouth to increase.

4. The device defined in claim 1, further including a removable tongue depressor, wherein said tongue depressor comprises:
   (a) a channel portion to fit said lower channel of said body; and
   (b) a flap portion, having upper and lower surfaces, attached to said channel portion and adapted to fit over and depress the tongue of said patient when said body is placed in said patient's mouth.

5. The device defined in claim 4, wherein said tongue depressor further comprises:
   (c) said flap portion includes a hollow interior;
   (d) at least one of said upper and lower surfaces of said flap portion defines a plurality of holes therethrough; and
   (e) means to connect the interior of said flap portion to the interior of said body.

6. The device defined in claim 4, wherein said lower surface of said flap portion is scalloped.

7. The device defined in claim 1, wherein at least one integral tongue depressor, having a flap portion with upper and lower surfaces, extends outward from an edge of said body.

8. The device defined in claim 7, wherein said integral tongue depressor further comprises:
   (a) said flap portion includes a hollow interior;
   (b) at least one of said upper and lower surfaces of said flap portion defines a plurality of holes therethrough; and
   (c) means to connect the interior of said flap portion to the interior of said body.

9. The device defined in claim 7, wherein said lower surface of said flap portion is scalloped.

10. The device defined in claim 1, wherein said body is formed of two separable and re-attachable sections so that said interior of said body may be accessed.

11. The device defined in claim 1, wherein said body is adapted to have saliva collecting tubes attached to said interior thereof.

12. The device defined in claim 11, wherein said saliva collecting tubes are perforated.

13. The device defined in claim 11, wherein said saliva collecting tubes may be shortened to a desired length.

14. The device defined in claim 1, wherein said communicating means includes a coupling on one end of said body.

15. The device defined in claim 14, wherein said coupling may be removably attached to an angle tube extending from said patient's mouth, said angle tube being connected to a suction hose.

16. The device defined in claim 1, wherein said body includes illumination means in the interior thereof.

17. The device defined in claim 16, wherein said illumination means includes a thermal cutout switch in operative association therewith.

18. A combination jaw rest and ejector system, comprising:
   (a) a generally hollow, closed, wedge-shaped body having longitudinal upper and lower channels formed on the sloped upper and lower edges thereof, said body and said channels being dimensioned such that said body may be inserted into one side of a patient's mouth, with several upper teeth of said patient removably fitting into said upper channel and with several lower teeth of said patient removably fitting into said lower channel, such that said body holds open said patient's mouth;
   (b) a plurality of holes defined through at least one side of said body;
   (c) communicating means to permit communication of said holes and the interior of said body with a source of vacuum; whereby, airborne liquid and solid materials may be drawn from said patient's mouth, through said communicating means, and to said source of vacuum;
   (d) illumination means disposed within said interior of said body; and
   (e) combination air flow/illumination switch means disposed in said communicating means to control the flow of air from said interior of said body and to activate and deactivate said illumination means.

19. The system defined in claim 18, wherein said switch means will cause some air to flow whenever said illumination means is activated.

20. An illuminated jaw rest, comprising:
   (a) a partially hollow, closed, wedge-shaped body having longitudinal upper and lower channels formed on the sloped upper and lower edges thereof, said body and said channels being dimensioned such that said body may be inserted into one side of a patient's mouth, with several upper teeth of said patient removably fitting into said upper channel and with several lower teeth of said patient removably fitting into said lower channel, such that said body holds open said patient's mouth; and
   (b) a plurality of holes defined through at least one side of said body; and
   illumination means disposed within said interior of said body whereby light is diffused through said holes.

* * * * *